(12) United States Patent
Roeder et al.

(10) Patent No.: US 8,877,549 B2
(45) Date of Patent: Nov. 4, 2014

(54) LOW TEMPERATURE DEPOSITION OF PHASE CHANGE MEMORY MATERIALS

(71) Applicant: Advanced Technology Materials, Inc., Danbury, CT (US)

(72) Inventors: Jeffrey F. Roeder, Brookfield, CT (US); Thomas H. Baum, New Fairfield, CT (US); Bryan C. Hendrix, Danbury, CT (US); Gregory T. Stauf, Branchburg, NJ (US); Chongying Xu, New Milford, CT (US); William Hunks, Waterbury, CT (US); Tianniu Chen, Rocky Hill, CT (US); Matthias Stender, Aurora, IL (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 14/223,500

(22) Filed: Mar. 24, 2014

(65) Prior Publication Data

US 2014/0206134 A1 Jul. 24, 2014

Related U.S. Application Data

(63) Continuation of application No. 13/610,928, filed on Sep. 12, 2012, now Pat. No. 8,679,894, which is a continuation of application No. 12/300,459, filed as application No. PCT/US2007/063832 on Mar. 12, 2007, now Pat. No. 8,288,198.

(60) Provisional application No. 60/800,102, filed on May 12, 2006.

(51) Int. Cl.
*H01L 51/40* (2006.01)
*H01L 51/00* (2006.01)

(52) U.S. Cl.
CPC .................................. *H01L 51/0002* (2013.01)
USPC .............. 438/99; 438/579; 438/602; 438/622

(58) Field of Classification Search
None
See application file for complete search history.

(56) References Cited

U.S. PATENT DOCUMENTS

2004/0197945 A1* 10/2004 Woelk et al. .................... 438/99

* cited by examiner

*Primary Examiner* — Kyoung Lee
(74) *Attorney, Agent, or Firm* — Hultquist, PLLC; Steven J. Hultquist; Maggie Chappuis

(57) ABSTRACT

A system and method for forming a phase change memory material on a substrate, in which the substrate is contacted with precursors for a phase change memory chalcogenide alloy under conditions producing deposition of the chalcogenide alloy on the substrate, at temperature below 350° C., with the contacting being carried out via chemical vapor deposition or atomic layer deposition. Various tellurium, germanium and germanium-tellurium precursors are described, which are useful for forming GST phase change memory films on substrates.

19 Claims, 1 Drawing Sheet

LOW TEMPERATURE DEPOSITION OF PHASE CHANGE MEMORY MATERIALS

CROSS-REFERENCE TO RELATED APPLICATIONS

This application is a continuation under the provisions of 35 U.S.C. §120 of U.S. patent application Ser. No. 13/610,928, filed Sep. 12, 2012, and issued on Mar. 25, 2014 as U.S. Pat. No. 8,679,894, which is a continuation under the provisions of 35 U.S.C. §120 of U.S. patent application Ser. No. 12/300,459 filed Nov. 11, 2008 (371(c) date, Dec. 22, 2008), and issued on Oct. 16, 2012 as U.S. Pat. No. 8,288,198, which is a U.S. national phase patent application under the provisions of 35 U.S.C. §371 of International Patent Application No. PCT/US2007/063832 filed Mar. 12, 2007, which in turn claims the benefit of U.S. Provisional Patent Application No. 60/800,102 filed May 12, 2006. The disclosures of all such applications are hereby incorporated herein by reference in their respective entireties, for all purposes.

BACKGROUND OF THE INVENTION

1. Field of the Invention

The present invention relates to low temperature deposition of phase change memory materials, by deposition techniques such as chemical vapor deposition and atomic layer deposition, to form microelectronic device structures.

2. Description of the Related Art

Phase Change Memory (PCM) refers to a novel memory technology based on chalcogenide materials that undergo a phase change via a heater and are read out as "0" or "1" based on their electrical resistivity, which changes in correspondence to whether the phase change material in the cell is in the crystalline or amorphous phase.

The chalcogenide materials used in PCM comprise a large number of binary, ternary, and quaternary alloys of a number of metals and metalloids. Examples include GeSbTe, GeSbInTe, and many others. As contained herein, the identification of compounds such as GeSbTe and GeSbInTe without appertaining stoichiometric coefficients or values will be understood as a general representation inclusive of all forms of such compounds containing the specified elements, and inclusive of all appertaining stoichiometric coefficients and values. For example, the reference to GeSbInTe includes $Ge_2Sb_2Te_5$, as well as all other stoichiometric forms of such compound GeSbInTe.

PCM devices require relatively pure chalconide material alloys, with well controlled composition. Current processes for making PCM devices utilize physical vapor deposition to deposit thin films of these chalconide materials. The thick planar structures of the current generation are well-served by PVD.

As device geometries shrink, the chalconide material must be deposited into vias in order to control the phase transition and the necessary heat transfer. Such implementation of chalconide materials can also be beneficial in improving reliability of small volume devices.

A major deficiency in the current art is the requirement of high deposition temperatures needed for conventionally employed alkyl (e.g., $Me_3Sb$, $Me_2Te$) or halide sources. These temperatures are typically well in excess of 300° C., and may for example be on the order of 500° C. Such high temperatures substantially exceed the thermal budget for device integration and can result in the evaporation of the chalcogenide, rendering the product PCM device deficient or even useless for its intended purpose.

The art continues to seek improvements in the art of PCM devices, including improvements in manufacturing techniques and improved precursors useful for forming memory device structures.

SUMMARY OF THE INVENTION

The present invention relates to systems and processes for deposition of phase change memory material on substrates, for fabrication of a phase change memory devices.

The invention relates in one aspect to a method of forming a phase change memory material on a substrate, comprising contacting the substrate with precursors for a phase change memory chalcogenide alloy under conditions producing deposition of the chalcogenide alloy on the substrate, wherein such conditions comprise temperature below 350° C. and such contacting comprises chemical vapor deposition or atomic layer deposition.

In another aspect, the invention relates to a method of forming a germanium-antimony-tellurium phase change memory material on a substrate, comprising contacting the substrate with precursors for a phase change memory germanium-antimony-tellurium alloy under conditions producing deposition of the germanium-antimony-tellurium alloy on the substrate, wherein such conditions comprise temperature below 350° C. and such contacting comprises chemical vapor deposition or atomic layer deposition, with the precursors comprising at least one halide precursor.

Yet another aspect of the invention relates to a system for fabricating a phase change memory device including a phase change memory material on a substrate, such system including a deposition tool adapted to receive precursors from precursor supply packages, and precursor supply packages containing precursors for forming a phase change memory chalcogenide alloy under conditions producing deposition of the chalcogenide alloy on the substrate, wherein such deposition tool is adapted for chemical vapor deposition or atomic layer deposition operation under conditions comprising deposition temperature below 350° C.

A further aspect of the invention relates to a system for fabricating a germanium-antimony-tellurium phase change memory device including a germanium-antimony-tellurium phase change memory material on a substrate, such system comprising a deposition tool adapted to receive precursors from precursor supply packages, and precursor supply packages containing germanium, antimony and tellurium precursors for forming a germanium-antimony-tellurium phase change memory chalcogenide alloy under conditions producing deposition of the chalcogenide alloy on the substrate, wherein the deposition tool is adapted for chemical vapor deposition or atomic layer deposition operation under conditions comprising deposition temperature below 350° C., and at least one of the precursor supply packages contains a halide precursor.

Additional aspects of the invention relate to PCM films formed in accordance with the present invention; corresponding devices; tellurium complexes, germanium complexes, germanium tellurides, and processes utilizing same for forming GST films; compositions including combinations of precursors for forming PCM films; and packaged precursors adapted for coupling to a deposition tool comprising such compositions, as hereinafter more fully described.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
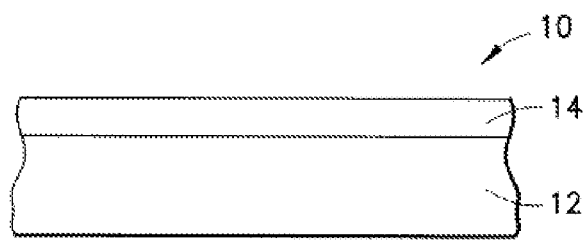
FIG. 1 is a schematic representation of a phase change memory device comprising a phase change memory material film formed on a substrate, according to one embodiment of the invention.

The present invention relates to deposition of phase change memory materials to form PCM devices.

More specifically, the invention in one aspect relates to chalcogenide alloys, and to their low temperature deposition e.g., by chemical vapor deposition (CVD) or atomic layer deposition (ALD), to form PCM devices. CVD and ALD methods are employed in the practice of the present invention to achieve scalability to large area wafers and for composition control. Preferred chalconide alloys include alloys including two or more of germanium, antimony and tellurium.

As used herein, the term "low temperature" means a temperature below 350° C. The temperature at which the PCM material is deposited is preferably less than 300° C., more preferably less than 250° C. and most preferably less than 225° C.

In one aspect, the invention relates to a method of forming a phase change memory material on a substrate, comprising contacting the substrate with precursors for a phase change memory chalcogenide alloy under conditions producing deposition of the chalcogenide alloy on the substrate, wherein such conditions comprise temperature below 350° C. and such contacting comprises chemical vapor deposition or atomic layer deposition.

The advantages of chemical vapor deposition and atomic layer deposition at low deposition temperature in the fabrication of PCM devices include substantial improvement of read/re-write times in small devices, as a result of the high conformality of the deposited PCM material.

Such method may further include fabricating said phase change memory material is into a phase change memory device.

The chalcogenide metal and metal alloy precursors that are advantageously used for forming PCM films and devices include:

(i) butyl- and propyl-substituted alkyl hydrides of the formula $R_xMH_{y-x}$ wherein: R is butyl or propyl, with R preferably being t-butyl or isopropyl; M is a metal having an oxidation state y, e.g., Ge, Sb or Te; x>1; and (y−x) may have a zero value;

(ii) butyl- and propyl-substituted alkyl halides of the formula $R_xMH_{y-x}$ wherein: R is butyl or propyl, with R preferably being t-butyl or isopropyl; X is F, Cl, or Br; M is a metal having an oxidation state y, e.g., Ge, Sb or Te; x>1; and (y−x) may have a zero value;

(iii) digermanes of the formula $Ge_2(R^1)_6$ wherein the $R^1$ substituents are the same as or different from one another, and each $R^1$ independently selected from among H, $C_1$-$C_8$ alkyl, $C_1$-$C_8$ fluroalkyl, $C_6$-$C_{12}$ aryl, $C_6$-$C_{12}$ fluoroaryl, $C_3$-$C_8$ cycloalkyl, and $C_3$-$C_8$ cyclo-fluoroalkyl, with illustrative digermanes including $Ge_2H_6$, $Ge_2Me_6$, $Ge_2Et_6$, $Ge_2iPr_6$, $Ge_2tBu_6$, $Ge_2(SiMe_3)_6$ and $Ge_2Ph_6$, wherein Me=methyl, Et=ethyl, iPr=isopropyl, Bu=butyl and Ph=phenyl;

(iv) digermanes of the formula $Ge_2(R^1)_4$ wherein the $R^1$ substituents are the same as or different from one another, and each $R^1$ is independently selected from among H, $C_1$-$C_8$ alkyl, $C_1$-$C_8$ fluroalkyl, $C_6$-$C_{12}$ aryl, $C_6$-$C_{12}$ fluoroaryl, $C_3$-$C_8$ cycloalkyl, and $C_3$-$C_8$ cyclo-fluoroalkyl, with illustrative digermanes including $Ge_2Ph$, wherein Ph=phenyl;

(v) ring compounds including Ge as a ring constituent, e.g., five-member ring compounds;

(vi) Ge(II) compounds of the formula $Ge(Cp(R^2)_5)_2$ wherein Cp is cyclopentadienyl having $R^2$ substituents on the cyclopentadienyl ring carbon atoms, wherein the $R^2$ substituents are the same as or different from one another, and each $R^2$ is independently selected from among H, $C_1$-$C_8$ alkyl, $C_1$-$C_8$ fluoroalkyl, $C_1$-$C_8$ alkylamino, $C_6$-$C_{12}$ aryl, $C_6$-$C_{12}$ fluoroaryl, $C_3$-$C_8$ cycloalkyl, and $C_3$-$C_8$ cyclo-fluoroalkyl;

(vii) Ge(II) compounds of the formula $Ge(R^3)_2$, wherein the $R^3$ substituents are the same as or different from one another, and each $R^3$ is independently selected from among silyl, silylalkyl and substituted silylalkyl, e.g., wherein each $R^3$ is —CH(SiMe_3)_2;

(viii) Sb compounds of the formula $Sb(R^4)_3$ wherein $R^4$ is phenyl, or substituted phenyl whose substituent(s) on the phenyl ring are independently selected from among H, $C_1$-$C_8$ alkyl, and $C_1$-$C_8$ fluroalkyl;

(ix) Sb and Te analogs of germanium compounds (iii), (iv), (v), (vi), and (vii);

(x) Ge and Te analogs of antimony compounds (viii); and (xi) $GeI_4$, $SbI_3$ and $TeI_2$.

It will be appreciated that the component metal species may have different oxidation states in the various above-mentioned compounds.

The above listing of precursors, in reference to the digermanes, germane ring compounds and Ge(II) compounds identified above, may further include corresponding analogs wherein Ge is replaced by Sb or Te. Likewise, the above listing of precursors, in reference to the Sb compounds identified above, may further include corresponding analogs wherein Sb is replaced by Ge or Te.

Various of the above compounds, e.g., antimony compounds of group (viii), are light-sensitive in character and amenable to light/UV-activated processes for PCM deposition. Such compounds thus may be exposed to radiation for activation during the deposition, involving visible light exposure or ultraviolet light exposure.

The deposition may be carried out in a chamber of a deposition reactor, as a deposition tool that is arranged and adapted for production of PCM products. The invention contemplates the provision of doping of the deposited PCM material, with dopant species that improve the character of the deposited material for PCM applications. For example, oxygen doping may be employed, or doping with other implanted species, to provide PCM films of superior character. The invention also contemplates the in situ doping of the PCM material at the time of its formation on the substrate.

A still further aspect of the invention relates to a system for fabricating a phase change memory device including a phase change memory material on a substrate, such system including a deposition tool adapted to receive precursors from precursor supply packages, and precursor supply packages containing precursors for forming a phase change memory chalcogenide alloy under conditions producing deposition of the chalcogenide alloy on the substrate, wherein such deposition tool is adapted for chemical vapor deposition or atomic layer deposition operation under conditions comprising deposition temperature below 350° C.

The chalcogenide metal and alloy precursors described above have been discovered to provide superior deposition when utilized in CVD and ALD processes, with lower deposition temperatures employed in the CVD or ALD process than have heretofore been achievable using physical vapor deposition techniques. Such lower temperature deposition capability in CVD and ALD processes is realized as a result of the chalcogenide metal or metal alloy compound undergoing beta hydrogen elimination reaction in the CVD and ALD deposition processes, e.g., involving iso-propyl and/or t-butyl groups. The digermane compositions benefit from the low bond energy of Ge—Ge. The Ge(II) compounds are easier to reduce than Ge(IV) compounds.

The chalcogenide metal or metal alloy precursors for the PCM material deposition may be provided in any suitable form, including solids, liquids and gases, and multiphase compositions, depending on the specific precursors involved. The precursors can be delivered to the deposition chamber, for carrying out CVD or ALD therein, by any suitable delivery techniques, dependent on their phase characteristics, required flow rate, temperature, etc. Co-reactants may be employed with the precursors to effect the CVD or ALD operation.

The precursor and co-reactant species can be supplied from material storage and dispensing packages of any suitable type, depending on the phase and the material characteristics of the precursor involved. For example, the storage and dispensing packages may include supply vessels of a type commercially available from ATMI, Inc. (Danbury, Conn., USA) under the trademarks SDS, VAC, SAGE or ProE-Vap. The storage and dispensing packages in preferred practice can comprise sub-atmospheric pressure systems providing improved safety and cost of ownership character, in relation to conventional high pressure material sources, such as the aforementioned packages available under the SDS, VAC and SAGE trademarks.

In such system and method, at least one of the precursors can be delivered for the contacting from a storage and dispensing vessel containing at least one of physical adsorbent, a gas low pressure regulator, a heat transfer structure, or an ionic liquid. The storage and dispensing vessel advantageously is adapted to contain precursor at sub-atmospheric pressure.

For example, the precursor when in a solid or liquid form can be volatilized to form a precursor vapor which then is flowed to the deposition chamber and contacted with the substrate on which the PCM device is to be fabricated. The substrate in such instance can be suitably heated, by a susceptor or other heating arrangement, whereby the contact between the precursor vapor and the substrate results in the deposition of a PCM material, e.g., in a film, on the substrate. As used in such context, the term "film" means a layer of the PCM material that is below 1 micrometer in thickness.

In the delivery operation associated with the CVD or ALD process, wherein the precursors are in a liquid state, separate bubblers or other delivery equipment can be employed for each precursor. Liquid injection of mixtures of precursors can be advantageously employed to manage disparate volatilities of the different precursors and to deliver precise volumetric flows of precursor medium having a desired composition. In the precursor delivery, the precursors may be utilized in the form of neat liquids, or precursor/solvent mixtures may be employed, in which the precursor is dissolved or suspended in a compatible solvent medium. Suitable solvents for such purpose can be identified by solubility and compatibility data for the precursor(s) of interest, or by routine solvent screening determinations, within the skill of the art, based on the disclosure herein.

The PCM material is deposited on the substrate by CVD or ALD techniques, in accordance with the invention.

When chemical vapor deposition is employed to form the PCM material layer on the substrate, continuous CVD in a thermal mode may be employed, with the CVD operation being conducted in a suitable CVD reactor chamber. The precursor vapor can be delivered in a carrier gas stream including the precursor vapor, and a carrier gas such as hydrogen, or other reducing gas, or an inert gas, or an oxidant, as may be desirable in a specific application.

When atomic layer deposition or pulsed deposition is used, a dose step involving introduction of the precursor vapor is alternated with injection into the deposition chamber of a co-reactant. The co-reactant can be of any suitable type, as effective to provide a PCM material layer of desired character on the substrate.

In one embodiment, the alternatingly introduced co-reactant is a hydrogen plasma, or other plasma co-reactant.

Alternatively, other activation techniques can be employed, such as ultraviolet (UV) radiation or other light source "tuned" to the precursor to effect the deposition of the desired PCM material. Light used for such purpose can be continuous with the precursor introduction, or may be dosed separately into the deposition chamber to avoid gas-phase reactions.

The pulsed introduction of reagents into the deposition chamber in atomic layer deposition operation can include introduction of a reductive co-reactant in alternation with the introduction of the metal or metal alloy precursor. The reductive co-reactant may for example include $GeH_4$.

The invention further contemplates use of a reductive co-reactant that is activatable by radiation exposure. Further, in ALD processes in accordance with the invention, the precursor for formation of the PCM material on the substrate is alternatingly pulsed into the deposition chamber. Thus, in instances in which the PCM material is deposited on a substrate in a pulsed introduction for contacting the substrate, it may be advantageous in some embodiments to utilize radiation to activate the PCM material and/or a co-reactant, e.g., to pulse the radiation source so that the PCM material or co-reactant are activated. Alternatively, if both PCM material and the co-reactant are radiation-activatable, then it may be desirable to maintain radiation generation and exposure throughout the deposition operation. As a still further variation, it may be desirable in some instances to pulse the radiation so that the radiation source is pulsed on when the precursor is not turned on.

The specific deposition conditions (e.g., temperature, pressure, flow rate, composition, etc.) for the CVD or ALD operation that is employed to form the PCM layer on the substrate can be readily determined within the skill of the art, based on the disclosure herein. CVD and ALD systems and techniques generally applicable to the present invention are more fully described in U.S. Provisional Patent Application 60/791,299 filed Apr. 12, 2006 for "PRECURSOR COMPOSITIONS FOR ATOMIC LAYER DEPOSITION AND CHEMICAL VAPOR DEPOSITION OF TITANATE DIELECTRIC FILMS," the disclosure of which hereby is incorporated herein by reference, in its entirety.

In another specific aspect, the invention relates to low temperature deposition of germanium-antimony-tellurium (Ge—Sb—Te, or "GST") material on substrates by a halide precursor approach.

More specifically, the invention in such aspect relates to a method of forming a germanium-antimony-tellurium phase change memory material on a substrate, comprising contacting the substrate with precursors for a phase change memory germanium-antimony-tellurium alloy under conditions producing deposition of the germanium-antimony-tellurium alloy on the substrate, wherein such conditions comprise temperature below 350° C. and such contacting comprises chemical vapor deposition or atomic layer deposition, with the precursors comprising at least one halide precursor.

Germanium, antimony and tellurium halides are volatile, and usefully employed for depositing GST thin films. In particular, their iodides are volatile and the corresponding metal-iodine bonds are weak. Accordingly, $GeI_4$, $SbI_3$ and $TeI_2$ are preferred halide source reagents for formation of GST films by CVD or ALD, e.g., using solid precursor delivery techniques.

Alternatively, one or two of the respective (Ge, Sb, Te) metals can be supplied from an iodide or other halide precursor compound(s), and the other one(s) of the metals can be supplied from alkyl metal compound(s). By way of specific illustrative example, the precursors can include $GeI_4$ and $TeI_2$ as halide precursors and $Sb(CH_3)_3$ as an alkyl precursor, to form the GST layer on the substrate. In such halide/alkyl precursor scheme, the alkyl(s) function as reducing agent(s) to eliminate iodo-methane, thereby enabling the achievement of clean GST films at low temperature.

The precursor delivery and deposition conditions can be readily determined, as appropriate for a given application of forming a GST material on a substrate, by simple empirical determination, to identify suitable temperatures, pressures, flow rates and concentrations to be employed for formation of suitable GST deposits on the substrate.

Thus, the invention contemplates a system for fabricating a germanium-antimony-tellurium phase change memory device including a germanium-antimony-tellurium phase change memory material on a substrate, such system comprising a deposition tool adapted to receive precursors from precursor supply packages, and precursor supply packages containing germanium, antimony and tellurium precursors for forming a germanium-antimony-tellurium phase change memory chalcogenide alloy under conditions producing deposition of the chalcogenide alloy on the substrate, wherein the deposition tool is adapted for chemical vapor deposition or atomic layer deposition operation under conditions comprising deposition temperature below 350° C., and at least one of the precursor supply packages contains a halide precursor.

Substrates in the general practice of the present invention can be of any suitable type, and may be doped or undoped, semiconducting, semi-insulating, or of other suitable character for the device structure of the PCM product. Useful substrates in specific applications may include silicon, sapphire, gallium arsenide, gallium nitride, silicon carbide, and the like.

Referring now to the drawings, FIG. 1 is a schematic representation of a phase change memory device 10 comprising a phase change memory material film 14 formed on a substrate 12, according to one embodiment of the invention. The film 14 may comprise a germanium-antimony-tellurium (GST) film, and the substrate may comprise any suitable substrate compatible with such film.

Figure 2:
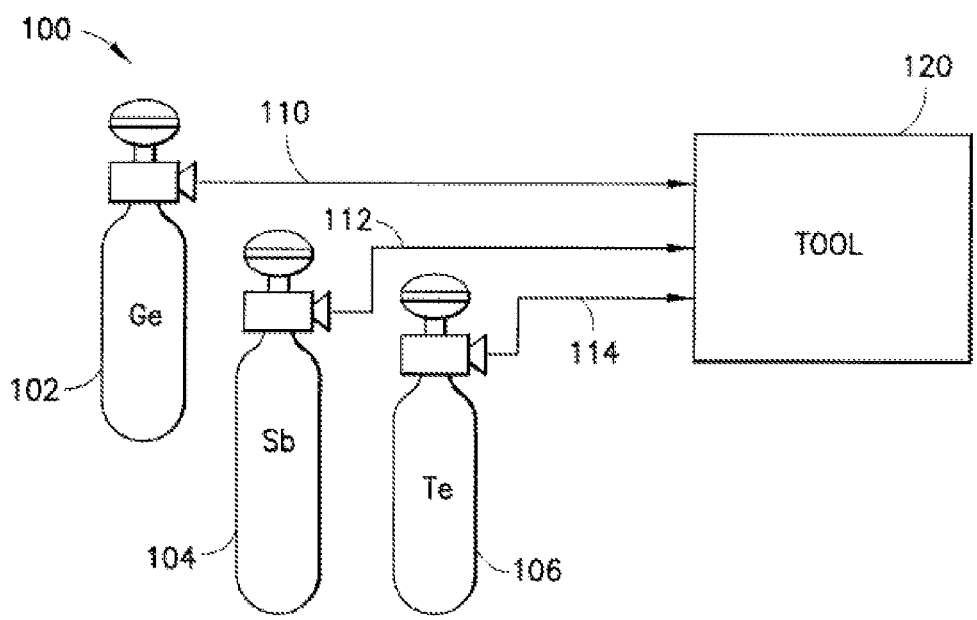
FIG. 2 is a schematic representation of a process installation including a deposition tool for depositing a phase change memory material on a substrate in accordance with one embodiment of the invention, from respective precursor supply packages of germanium precursor, antimony precursor and tellurium precursor.

FIG. 2 is a schematic representation of a process installation 100 including a deposition tool 120 for depositing a phase change memory material on a substrate in accordance with one embodiment of the invention, from respective precursor supply packages 102, 104 and 106 of germanium precursor (in vessel 102 labeled "Ge"), antimony precursor (in vessel 104 labeled "Sb") and tellurium precursor (in vessel 106 labeled "Te"). Each of the precursor supply packages includes a storage and dispensing vessel equipped with a valve head assembly including a flow control valve that may be manually or automatically operated, to dispense the appertaining precursor on demand at a desired flow rate.

As illustrated, each of the precursor supply vessels is coupled with flow circuitry for delivery of the dispensed precursor to the tool 120. Thus, the germanium precursor supply package 102 is coupled to the tool by line 110, the antimony precursor supply package 104 is coupled to the tool by line 112, and the tellurium precursors supplied package 106 is coupled to the tool by line 114. The tool can comprise a chemical vapor deposition (CVD) tool, an atomic layer deposition (ALD) tool, or other suitable tool adapted to receive the respective precursors and to form a PCM alloy film on a substrate, in the fabrication of a corresponding PCM device.

Another aspect of the invention relates to dopants in GeSbTe semiconductors, which can be formed in polycrystalline form and thereby accommodate a wider range of stoichiometries and dopants than typical semiconductors. Doping with nitrogen from levels of a few tenths of 1% to a few percent can be beneficial to properties of such materials in specific applications. Although the following discussion is directed primarily to nitrogen as the dopant species, it will be appreciated that the invention is not thus limited, and extends to the use of other dopant species.

Doping may be carried out by use of a reactant gas such as ammonia, or a vaporizable liquid such as an amine, to introduce nitrogen into the film. The reaction gas may be introduced separately, as a co-reactant, or it may be used as a carrier for the precursor(s), in which case it may also act as a stabilizing agent for the precursor. If this reactant gas reacts in the gas phase with the precursor(s), it may be necessary to pulse it alternately with the precursor(s), optionally with purge steps between pulses. Such pulsing may also be beneficial if it is desirable to have non-homogeneous layers, in order to achieve different dopant concentrations in contact with one or more electrodes for physical (sticking layer) or electrical (fermi layer adjustment) purposes.

Doping may also be affected by incorporation of nitrogen from a precursor. Process adjustments, such as conducting the deposition in certain "process windows" of reactor pressure, temperature, and/or gas flow can be employed to control the amount of N incorporated, thereby enabling adjustment of doping parameters. Specific precursors for one or more of Ge, Sb and Te materials may be employed for such purpose.

In another approach, specific co-reactants are employed to induce reaction pathways with one or more of the precursors that lead to the desired level of N incorporation. By way of example, use of $NH_3$ as a coreactant can be employed to enable lower temperature deposition and to promote N incorporation into the GST layer, compared to using $H_2$ as a co-reactant.

Another aspect of the invention relates to tellurium complexes with beta-diketiminate ligands, which overcome the problems that many tellurium precursors used in deposition applications are very oxygen-sensitive and light-sensitive, and have an unpleasant odor. By base stabilization with beta-diketiminate ligands, a tellurium precursor is obtained of a highly stable character with improved handling and shelf life characteristics, reduced odor, and sufficient volatility for deposition applications.

The tellurium diketiminate complexes of the invention can be used for CVD/ALD to form Te or Te-containing films. These compounds can be used in combination with Ge- and/ or Sb-compounds to produce Te—Ge—, Te—Sb— or Ge—Sb—Te films in varied compositions. A general procedure to synthesize diketiminate ligands has been described in the literature, but such procedure is disadvantageous, since very bulky aryl substituents on the coordinating nitrogen atoms are required.

In contrast, we have discovered that smaller alkyl ligands as iso-propyl, n-butyl, tert-butyl or amine-substituted alkyl groups, as for example ethylene-dimethylamine, can be advantageously used to produce superior tellurium diketiminate precursors for CVD/ALD applications. Smaller substituents on the nitrogen donor atoms provide sufficient volatility to form good films at low temperature.

The ligands L can be used as the lithium salt or in a free imine form to synthesize the desired Te complexes. The lithium salt of the ligand can be reacted with $TeX_4$ (wherein X=Cl, Br, I) to generate $LTeX_3$ by salt elimination, which can then be reacted with either a lithium or a Grignard reagent to produce $LTeR_3$ (wherein R=alkyl, aryl, amide, silyl).

Alternatively the free imine form of the ligand L can be reacted with a tellurium organic compound such as $TeMe_4$ to produce the desired Te species $LTeMe_3$ by methane elimination. The diketiminate ligands provide very effective base stabilization of the reactive metal center tellurium. The invention therefore provides a new class of Te complexes that provide greater stability and shelf life, while retaining sufficient volatility to form superior Te films via CVD/ALD at low temperatures.

The tellurium complexes of the invention have the formulae (I) and (II):

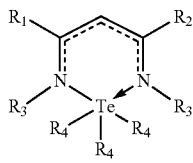

(I)

wherein $R_1$, $R_2$ and $R_3$ they be the same as or different from one another, and each is independently selected from $C_1$-$C_6$ alkyl, $C_6$-$C_{10}$ aryl, silyl and $C_1$-$C_{12}$ alkylamine (which includes both monoalkylamine as well as dialkylamine); and

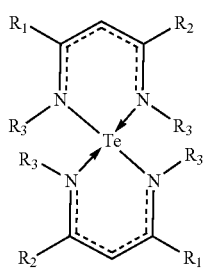

(II)

wherein $R_1$, $R_2$ and $R_3$ they be the same as or different from one another, and each is independently selected from $C_1$-$C_6$ alkyl, $C_6$-$C_{10}$ aryl, silyl and $C_1$-$C_{12}$ alkylamine (which includes both monoalkylamine as well as dialkylamine).

The beta-diketiminate ligands may for example be synthesized by the following procedure:

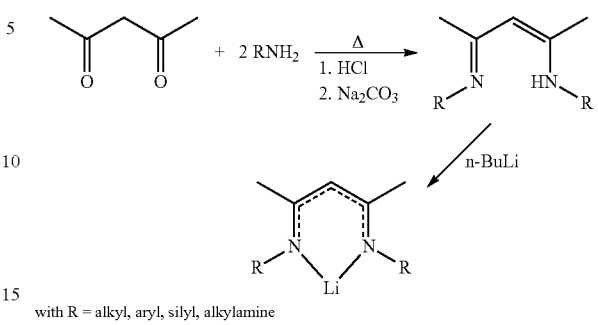

with R = alkyl, aryl, silyl, alkylamine

The tellurium complexes then can be synthesized by the following reaction:

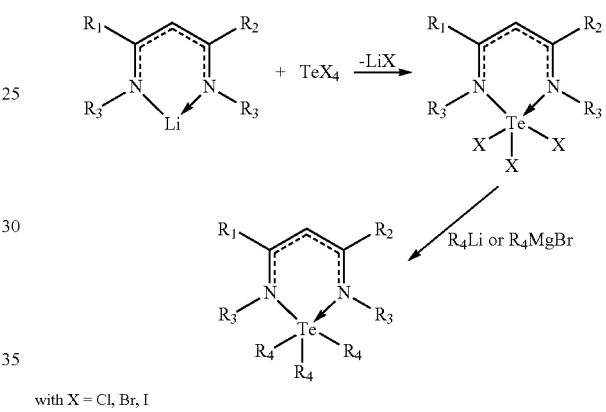

with X = Cl, Br, I
$R_1$, $R_2$, $R_3$, $R_4$ = alkyl, aryl, silyl, alkylamine or alternatively by the following synthesis reaction:

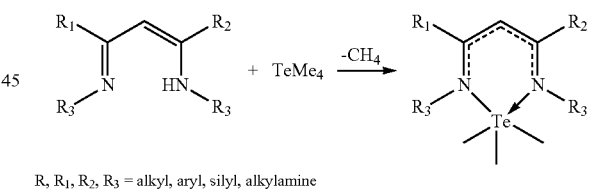

R, $R_1$, $R_2$, $R_3$ = alkyl, aryl, silyl, alkylamine or by the following synthesis reaction:

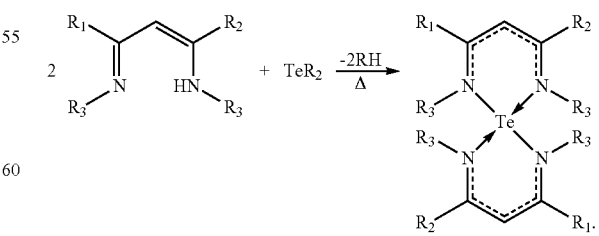

R, $R_1$, $R_2$, $R_3$ = alkyl, aryl, silyl, alkylamine

The tellurium complexes of the invention are usefully employed as CVD/ALD precursors for deposition of tellurium-containing thin films, e.g., by liquid injection of neat precursor material, or in organic solvent or by direct evaporation.

The invention in another aspect relates to germanium complexes and their use in CVD/ALD for forming germanium-containing films, e.g., GST films, wherein the germanium complexes are selected from among:

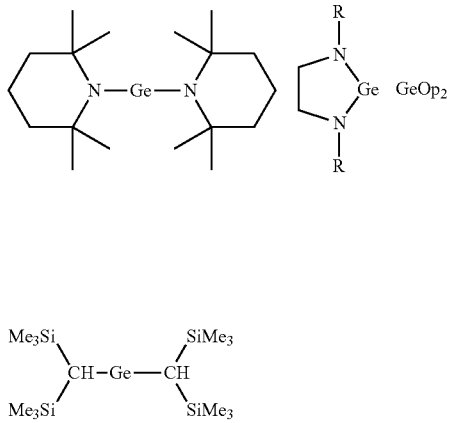

wherein the R groups in the second formula may be the same as or different from one another, and each is independently selected from among H, $C_1$-$C_6$ alkyl, $C_6$-$C_{10}$ aryl, $C_3$-$C_8$ cycloalkyl, heteroatom groups, and other organo groups.

Another aspect of the invention relates to digermane and strained ring germanium precursors for CVD/ALD of germanium-containing thin films. Previously employed germanium precursors such as germane that have been used for forming GST (germanium-antimony-tellurium) films for phase change memory devices require very high temperature deposition conditions. This in turn makes it difficult to form a pure $Ge_2Sb_2Te_5$ phase material. The present invention overcomes this deficiency in the provision of precursors having a high vapor pressure at ambient conditions, which are useful to deposit germanium-containing films at temperatures below 300° C.

Germanium-germanium bonds are inherently weak (~188 kJ/mole) and become less stable with electron withdrawing substituents such as chlorine or $NMe_2$. Such bonds can readily dissociate to form $R_3Ge$ radicals under UV photolysis or thermolysis, or by chemical oxidation using peroxides, ozone, oxygen or plasma. Commercially available digermanes include hydride, methyl, phenyl, or ethyl groups that require high temperatures for decomposition and the resulting films are often contaminated with carbon residues.

We have overcome such deficiency by the provision of germanium complexes using as ligands isopropyl, isobutyl, benzyl, allyl, alkylamino, nitriles, or isonitriles to achieve complexes that enabled the deposition of pure germanium metal films at low temperatures. In addition, the invention contemplates strained-ring germanium complexes (e.g., germacyclobutane) that can undergo thermal ring opening to generate a diradical intermediate that readily dissociates to germylene fragments. The bond dissociation energy of the strained Ge—C bond (63 kcal/mol) is considerable lower than Ge—$CH_3$ (83 kcal/mol), thereby enabling lower temperature film deposition of germanium to be achieved, than has been achievable with the aforementioned conventional germanium precursors.

The germanium complexes of the invention include those of formulae (I)-(III) below:

(I) alkyldigermanes of the formula

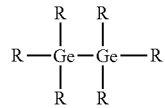

wherein each R may be the same as or different from the others, and each is independently selected from among isopropyl, isobutyl, benzyl, allyl, alkylamino, nitriles, and isonitriles;

(II) alkyl(dialkylamino)germanes of the formula

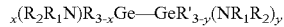

wherein each R may be the same as or different from the others, and each is independently selected from among isopropyl, isobutyl, benzyl, allyl, alkylamino, nitriles, and isonitriles; and (III) strained-ring germane complexes of the formula:

wherein each of $R_1$, $R_2$, $R_3$ and $R_4$ may be the same as or different from the others, and each is independently selected from among H, $C_1$-$C_6$ alkyl, $C_6$-$C_{10}$ aryl, $C_3$-$C_8$ cycloalkyl, or a heteroatom group.

The complexes (I) can be synthesized, by way of example, according to the following synthesis process:

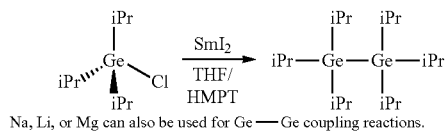

Na, Li, or Mg can also be used for Ge—Ge coupling reactions.

or by the following synthesis:

or by a synthesis such as the following:

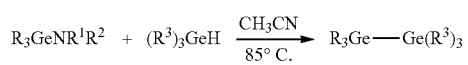

or a synthesis procedure such as:

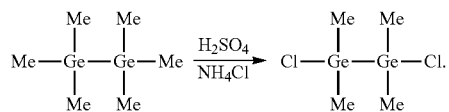

The germanium complexes of formula (II) can be formed by the following illustrated procedure:

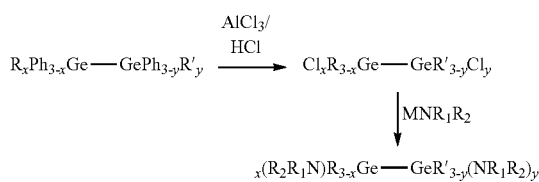

Illustrative synthesis processes that can be employed for forming germanium complexes of formula (III) includes the following:

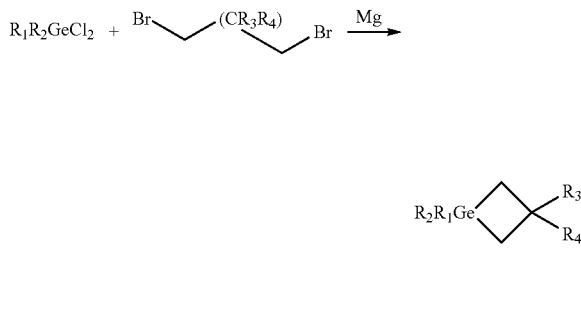

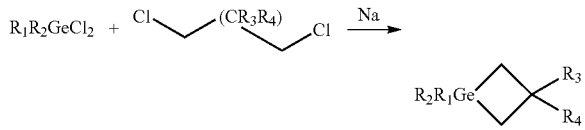

The strained ring alkylgermanes are usefully employed as CVD/ALD precursors for forming germanium-containing thin films on substrates involving reactions such as those illustratively shown below.

Strained ring alkylgermanes as CVD/ALD precursors for thin metal films

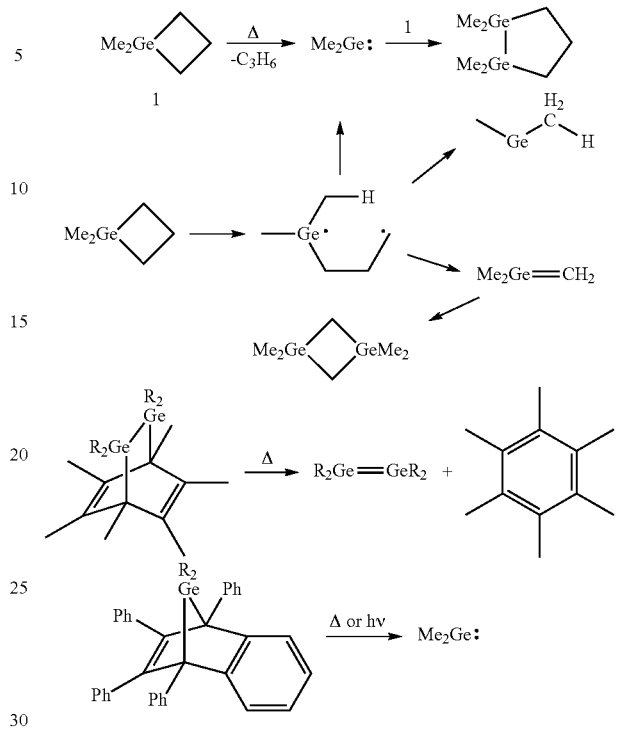

Another aspect of the invention relates to a single-source precursor for germanium and tellurium, as useful in the formation of GST films. Such single-source of germanium telluride precursors may be used in combination with an antimony precursor for GST film formation, optionally with co-reactants as may be desirable to provide films of appropriate stoichiometry for a given application.

The germanium telluride complexes of the invention in one aspect include dialkylgermanetellurones. Suitable dialkylgermanetellurones can be synthesized by oxidative addition reaction of germanium (II) dialkyls with elemental tellurium powder in a solvent medium such as tetrahydrofuran (THF). In some instances so it may be desirable to conduct the reaction in the absence of light, depending on the light-sensitivity of the product germanium-tellurium complex. An illustrative synthesis procedure is set out below:

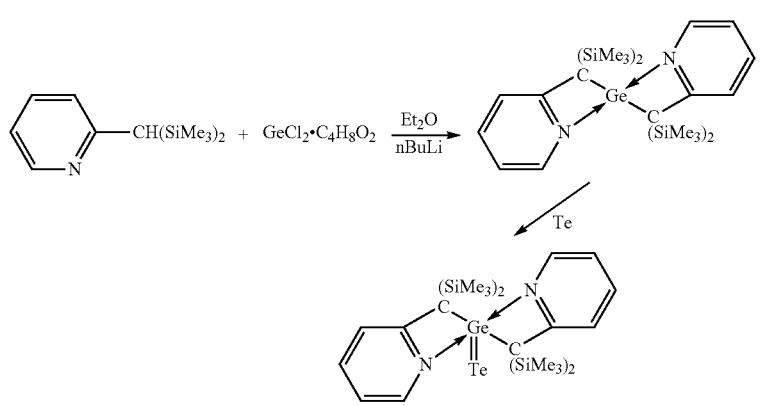

The single-source Ge—Te precursors of the invention can be advantageously used to facilitate lower temperature deposition processes or to increase GST film growth rates in specific applications.

Germanium tellurides of the invention, in another embodiment, can be formed by the following synthesis procedure:

Germanium telluride ALD/CVD precursors

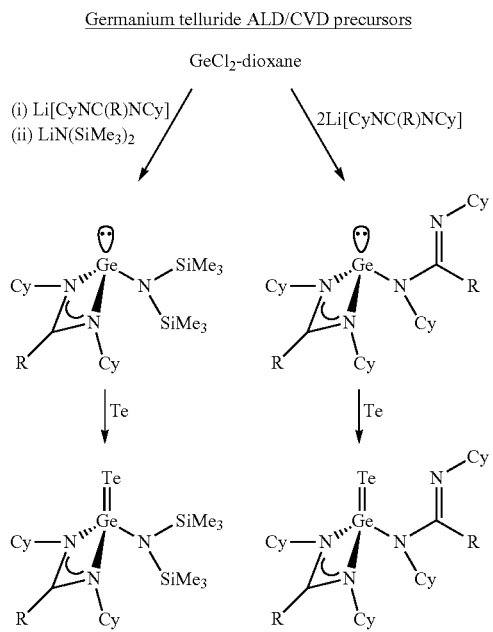

Other germanium telluride complexes can be formed by the following synthesis process:

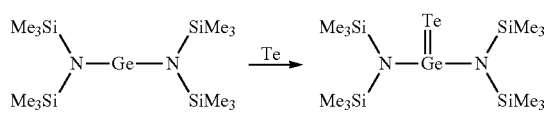

or by the following generalized reactions:

wherein E is tellurium; M is Li, Na, or K, X is chlorine, bromine or iodine; and the R and R' groups may be the same as or different from one another, and each is independently selected from among H, $C_1$-$C_6$ alkyl, $C_6$-$C_{10}$ aryl, $C_3$-$C_8$ cycloalkyl, heteroatom groups, and other organo groups.

One Ge—Te complex of the invention is:

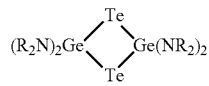

wherein each of the R substituents may be the same as or different from one another, and is independently selected from among H, $C_1$-$C_6$ alkyl, $C_6$-$C_{10}$ aryl, $C_3$-$C_8$ cycloalkyl, heteroatom groups, and other organo groups.

It will therefore be seen that the present invention contemplates a variety of precursors suitable for use in forming phase change memory films, e.g., GST films, and that the various precursors of the invention include precursors enabling deposition of films via CVD/ALD processes at temperatures below 300° C., as well as Ge—Te precursors affording substantial advantage in forming germanium- and tellurium-containing films.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method of forming a germanium-containing film on a substrate, comprising use of a Ge(II) compound of the formula $Ge(Cp(R^2)_5)_2$ wherein Cp is cyclopentadienyl having $R^2$ substituents on the cyclopentadienyl ring carbon atoms, wherein the $R^2$ substituents are the same as or different from one another, and each $R^2$ is independently selected from among H, $C_1$-$C_8$ alkyl, $C_1$-$C_8$ fluoroalkyl, $C_1$-$C_8$ alkylamino, $C_6$-$C_{12}$ aryl, $C_6$-$C_{12}$ fluoroaryl, $C_3$-$C_8$ cycloalkyl, and $C_3$-$C_8$ cyclo-fluoroalkyl, in chemical vapor deposition or atomic layer deposition.

2. The method of claim 1, wherein said chemical vapor deposition or atomic layer deposition is carried out at temperature below 350° C.

3. The method of claim 1, wherein said chemical vapor deposition or atomic layer deposition is carried out at temperature below 300° C.

4. The method of claim 1, further comprising use of an antimony precursor.

5. The method of claim 4, further comprising use of a tellurium precursor.

6. The method of claim 5, wherein chemical vapor deposition or atomic layer deposition is employed to form a phase change memory material.

7. The method of claim 6, comprising fabricating the phase change memory material into a phase change memory device.

8. The method of claim 1, wherein the method of forming a germanium-containing film on a substrate comprises use of the Ge(II) compound in chemical vapor deposition.

9. The method of claim 8, wherein the chemical vapor deposition comprises delivering the Ge(II) compound to the substrate in a carrier gas stream including a vapor of the Ge(II) compound.

10. The method of claim 1, wherein the method of forming a germanium-containing film on a substrate comprises use of the Ge(II) compound in atomic layer deposition.

11. The method of claim 1, wherein at least one $R^2$ is $C_1$-$C_8$ alkyl.

12. The method of claim 1, wherein at least one $R^2$ is $C_1$-$C_8$ fluoroalkyl.

13. The method of claim 1, wherein at least one $R^2$ is $C_1$-$C_8$ alkylamino.

14. The method of claim 1, wherein at least one $R^2$ is $C_6$-$C_{12}$ aryl.

15. The method of claim 1, wherein at least one $R^2$ is $C_6$-$C_{12}$ fluoroaryl.

16. The method of claim 1, wherein at least one $R^2$ is $C_3$-$C_8$ cycloalkyl.

17. The method of claim 1, wherein at least one $R^2$ is $C_3$-$C_8$ cyclo-fluoroalkyl.

18. The method of claim 1, wherein at least one $R^2$ is H.

19. The method of claim 1, wherein the Ge(II) compound is dissolved or suspended in a compatible solvent medium.

* * * * *